(12) United States Patent
Homman et al.

(10) Patent No.: US 8,076,341 B2
(45) Date of Patent: Dec. 13, 2011

(54) COMPOUNDS AND USE THEREOF

(75) Inventors: Mohammed Homman, Nacka (SE); Robert Engovist, Solna (SE); Cecilia E Söderberg-Nauclér, Bromma (SE); Jan Bergman, Spånga (SE)

(73) Assignee: Vironova AB, Nacka (SE)

( * ) Notice: Subject to any disclaimer, the term of this patent is extended or adjusted under 35 U.S.C. 154(b) by 514 days.

(21) Appl. No.: 12/161,081

(22) PCT Filed: Jan. 22, 2007

(86) PCT No.: PCT/SE2007/050033
§ 371 (c)(1),
(2), (4) Date: Oct. 9, 2008

(87) PCT Pub. No.: WO2007/084073
PCT Pub. Date: Jul. 26, 2007

(65) Prior Publication Data
US 2009/0318458 A1   Dec. 24, 2009

(51) Int. Cl.
*A61K 31/497* (2006.01)
*A61K 31/4965* (2006.01)
*C07D 471/00* (2006.01)

(52) U.S. Cl. ......... 514/252.11; 514/255.05; 514/255.06; 514/252.1; 544/343

(58) Field of Classification Search ............... 514/252.1, 514/255.05, 255.06; 544/343
See application file for complete search history.

(56) References Cited

FOREIGN PATENT DOCUMENTS
EP  0 238 459  9/1987

OTHER PUBLICATIONS

Harmenberg, J., et al. "Antiherpesvirus Activity and Mechanism of Action of Indolo-(2,3-*b*) Quinoxaline and Analogs." *Antimicrobial Agents and Chemotherapy* (1988) vol. 32, No. 11, pp. 1720-1724.
Collino, F., et al. "Basi di Mannich A Struttura Dipiperidnica Dotate di Attivita' Farmacologica." *Bolletino Chimico Farmaceutico* (1982) vol. 121, No. 8, pp. 408-421.
Patani, George A., et al. Biososterism: A Rational Approach in Drug Design. Chem. Rev. 1996, 96, pp. 3147-3176. Dec. 19, 1996.

*Primary Examiner* — Shengjun Wang
(74) *Attorney, Agent, or Firm* — Ladas & Parry LLP

(57) ABSTRACT

A compound of formula (I) wherein $R^1$ is selected from H, F, Cl, Br, $CF_3$, $C_1$-$C_6$ alkoxy and OH; $R^2$ is selected from H and $C_1$-$C_6$ alkyl; n is 1-12; m is 0 or 1; Y is selected from $CH_2$, $NR^3$, $(NR^3R^4)$+X, O and S; $R^3$ and $R^4$ are independently selected from H and $C_1$-$C_4$ alkyl; and X" is selected from phannaceutically acceptable anions. A method of preparing the compound, its use as a pharmaceutical, and a method of treatment.

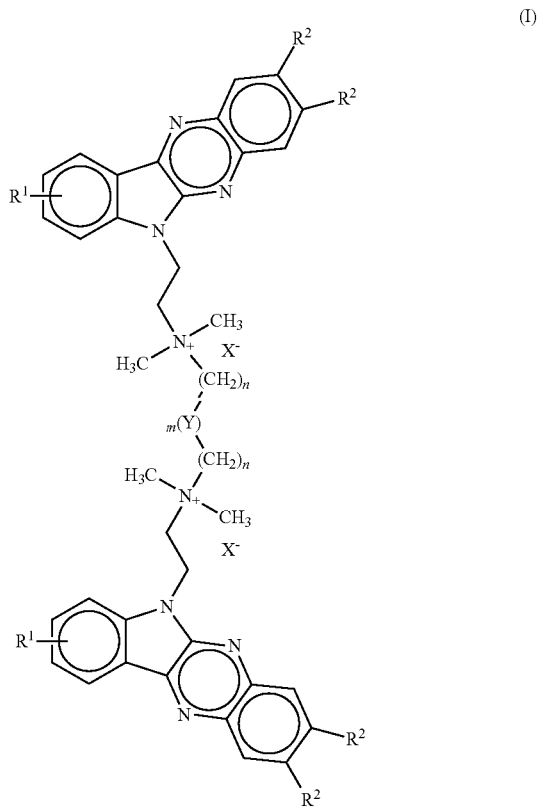

14 Claims, No Drawings

COMPOUNDS AND USE THEREOF

TECHNICAL FIELD OF THE INVENTION

The present invention relates to novel indoloquinoxaline derivatives, to methods for preparing them as well as to their pharmaceutical use. In particular, the invention relates to novel indoloquinoxaline derivatives and their use in the treatment of viral infections.

BACKGROUND OF THE INVENTION

As is well-known, viruses are the etiologic cause of many, sometimes life-threatening, diseases of both humans and animals. For example, herpes viruses such as herpes simplex 1 (HSV-1), herpes simplex 2 (HSV-2), cytomegalovirus (CMV), Epstein-Barr virus (EBV), varicella zoster virus (VZV) and human herpes virus 6 (HHV 6) are associated with many common viral illnesses.

Human CMV (HCMV) infection is a life-long affliction which can result in morbidity and mortality. The pathologies associated with HMCV include microcephaly, heptosplenomegaly, jaundice, encephalitis, infections of the newborn infants or fetuses in utero, and infections of immunocompromised hosts.

For several reasons, increasing numbers of persons are at risk for HCMV infection, and presently an estimated 80% of adults in the United States are infected with HCMV. A particularly susceptible group is those of weakened immune system, such as AIDS patients, where HCMV infection may cause retinitis, gastritis and pneumonitis. Also, HCMV-induced pneumonias or hepatitis are frequent and serious complications of bone marrow transplants.

European patent EP 0 238 459 relates to substituted indoloquinoxalines having the general formula

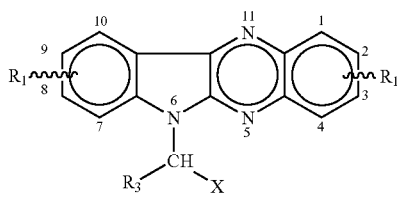

wherein $R_1$ represents hydrogen or one or several, preferably 1 to 4, similar or different substituents in the positions 1-4 and/or 7-10, selected from halogen, preferably Br, lower alkyl/alkoxy group having not more than 4 carbon atoms, trifluoromethyl group, trichloromethyl group; X is a group —$(CH_2)_n$—$R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide.

However, it is clear that there still exists an urgent need for new medicaments having antiviral efficacy, in particular against herpes viruses such as HMCV, and an object of the present invention is to provide compounds fulfilling this need.

SUMMARY OF THE INVENTION

According to a first aspect the invention provides a compound according to formula (I)

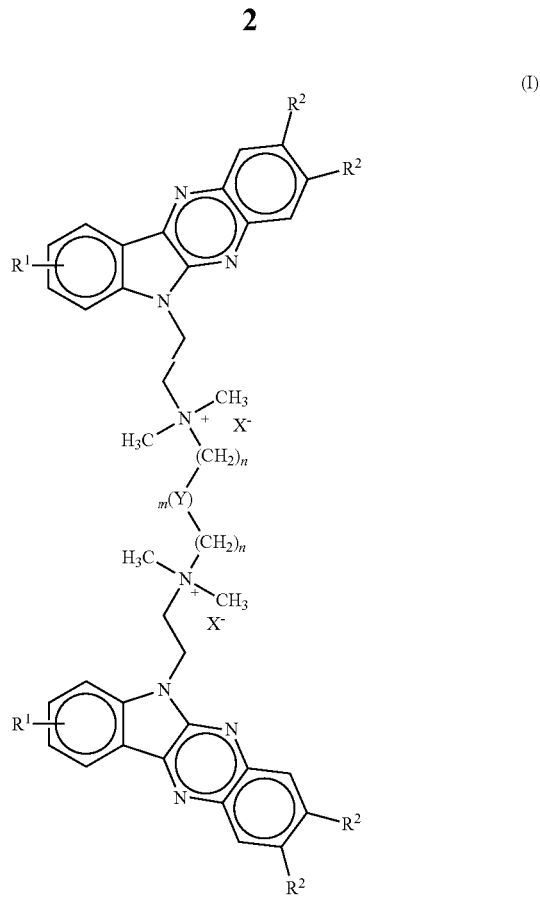

wherein
$R^1$ is selected from H, F, Cl, Br, $CF_3$, $C_1$-$C_6$ alkoxy and OH;
$R^2$ is selected from H and $C_1$-$C_6$ alkyl;
n is 1-12;
m is 0 or 1; and
Y is selected from $CH_2$, $NR^3$, $(NR^3R^4)^+X^-$, O and S;
$R^3$ and $R^4$ are independently selected from H and $C_1$-$C_4$ alkyl; and
$X^-$ is selected from pharmaceutically acceptable anions.

According to another aspect, a method of preparing a compound according to formula (I) is provided, by reacting a compound of formula (II)

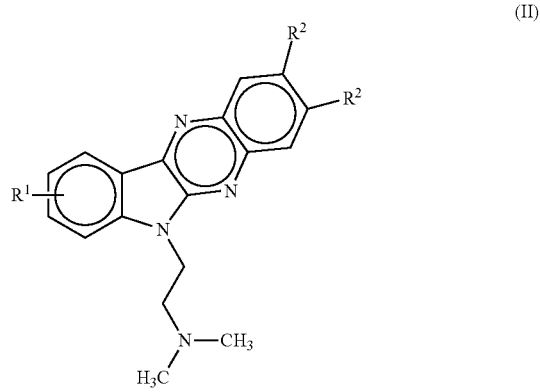

with a compound of formula (III)

$$L(CH_2)_n(Y)_m(CH2)_nL \qquad (III)$$

wherein $R^1$, $R^2$, Y, m and n are as defined herein above in respect of formula (I); and L is a leaving group;

in a solvent or mixture of solvents.

According to a still further aspect the invention provides a pharmaceutical composition comprising a compound according to formula (I) in association with at least one pharmaceutically acceptable excipient.

According to a one aspect of the invention, the pharmaceutical composition is an antiviral composition suitable for the treatment of a viral infection.

Further aspects of the invention as well as embodiments thereof are as defined in the claims.

DETAILED DESCRIPTION OF THE INVENTION

In one embodiment of the present invention, $R^1$ in formula (I) is selected from H, F, Cl, Br, $CF_3$, $OCH_3$ and OH.

Furthermore, in one embodiment of the invention, $R^2$ in formula (I) is selected from H and and $C_1$-$C_4$ alkyl, e.g. H and $C_1$-$C_3$ alkyl, such as H and $CH_3$.

The counterion $X^-$ in formula (I) may be any suitable pharmaceutically acceptable anion, such as $Cl^-$, $Br^-$, methanesulfonate, toluenesulfonate, acetate, citrate and maleate.

The index n in formula (I) may be selected from any value between 1 and 12, such as 2-10, or 4-10, e.g. 4-8; or 1-6, e.g. 1-3.

The compound of formula (II), used in preparing the compound of the invention, may itself be prepared as generally taught in EP 0 238 459 as well as in U.S. Pat. No. 4,990,510 which patents are both incorporated herein by reference.

The compound of formula (III), viz. $L(CH_2)_n(Y)_m(CH2)_n L$, may be synthesized by methods well-known to the person skilled in the art, or may be purchased from chemical suppliers.

The leaving group L of formula (III) may suitably be selected from e.g. Cl, Br, methanesulfonyl and toluenesulfonyl, although the skilled person will realise that also other leaving groups may be contemplated.

The solvent system used should be one wherein the reactants are soluble at the selected conditions of the reaction and should suitably be such as to favour the reaction leading to the desired product. As an example, one or several of a polar aprotic or protic solvent may be selected, such as acetonitril, THF, methanol, ethanol, isopropanol, ethyl acetate and methyl acetate. It is well within the knowledge of the skilled person to select such solvent system as well as suitable conditions of the reaction.

The compounds of the invention are useful as antiviral agents and thus, according to one aspect of the invention, an antiviral pharmaceutical composition is provided comprising a compound of formula (I) and at least one pharmaceutically acceptable excipient.

In one embodiment of the invention, the pharmaceutical composition is for the treatment of a virus selected from herpes viruses, such as herpes simplex 1 (HSV-1), herpes simplex 2 (HSV-2), cytomegalovirus (CMV), Epstein-Barr virus (EBV), varicella zoster virus (VZV) and human herpes virus 6 (HHV 6).

In one embodiment of the invention, the virus is a human cytomegalovirus.

The pharmaceutically acceptable excipients may be for example, vehicles, adjuvants, carriers or diluents, such as are well-known to the person skilled in the art and as described e.g. in Remington: The Science and Practice of Pharmacy, 21th ed., Mack Printing Company, Easton, Pa. (2005). Further, it is contemplated that the pharmaceutical composition of the invention, in addition to a compound of formula (I), may contain also other therapeutically active substances, e.g. other antiviral agents.

The pharmaceutical composition of the invention may be administered parenterally or orally and may be used in a local or systemic antiviral treatment of a vertebrate in need of such treatment, e.g. a bird or a mammal, such as a human or an animal such as a domestic animal or a farm animal. It is contemplated that a pharmaceutical composition of the invention may be administered together with other, compatible drugs, such as another antiviral drug in multidrug therapy.

Herein below the invention is further illustrated by examples that should however not be construed as limiting the invention, the scope of which is defined by the claims. It is noted that the numbering of each one of the two ring systems is the same as for the general formula of the substituted indoloquinoxaline of European patent EP 0 238 459, as shown herein above.

EXAMPLES

Preparation of Inventive Compounds

NMR spectra were recorded in DMSO-$d_6$ solutions at room temperature and using the signal from DMSO-$d_6$ ($^1$H: $\delta$ =2.50 ppm; $^{13}$C: $\delta$=39.5) as internal standard, on a Bruker DPX 300 (300 MHz) spectrometer. Values of $\delta$ are given in ppm. Solvents were of analytical grade and were used as received from the supplier.

Example 1

Synthesis of Alkylene Dimers

General Procedure (10 mmol Scale)

B-220 (formula II, $R^1$=H, $R^2$=$CH_3$, or derivatives thereof), dihaloalkane and acetonitrile were heated (at reflux or at 70° C.) for 15 h. The solid thus formed was isolated by filtration, washed with acetonitrile and dried.

1a) $R^1$=H, $R^2$=$CH_3$, n=3, m=0, $X^-$=$Br^-$

Yield: 70%; 1H-NMR $\delta$8.34 (d, 1H), 7.94 (m, 2H), 7.77 (m, 2H), 7.43 (t, 1H), 4.93 (br. s, 2H), 3.86 (br. s, 2H), 3.54 (br. s, 2H), 3.27 (s, 6H), 2.39 (s, 6H), 1.77 (br. s, 2H), 1.28 (br. s, 2H).

1b) $R^1$=H, $R^2$=$CH_3$, n=5, m=0, $X^-$=$Br^-$

Yield: 49%; 1H-NMR $\delta$8.35 (d, 1H), 8.00 (s, 1H), 7.92 (d, 1H), 7.80 (m, 2H), 7.45 (t, 1H), 4.91 (t, 2H), 3.85 (t, 2H), 3.49 (m, 2H), 3.24 (s, 6H), 2.48 (s, 3H), 2.45 (s, 3H), 1.69 (m, 2H), 1.17 (s, 6H).

1c) $R^1$=9-Br, $R^2$=$CH_3$, n=3, m=0, $X^-$=$Br^-$

Yield: 73%; 1H-NMR $\delta$8.39 (s, 1H), 8.08-7.81 (m, 3H), 7.73 (s, 1H), 5.16 (br. s, 2H), 3.69 (br. s, 2H), 3.43 (br. s, 2H), 3.25 (s, 6H), 2.39 (s, 3H), 2.37 (s, 3H), 1.88 (br. s, 2H), 1.32 (br. s, 2H).

1d) $R^1$=9-Cl, $R^2$=H, n=3, m=0, $X^-$=$Br^-$ $^{13}$C-NMR DMSO-$d_6$ $\delta$: 21.6 (t), 25.2 (t), 35.3 (t), 50.8 (q), 59.0 (t), 63.3 (t), 112.6 (d), 120.4 (s), 121.6 (d), 126.1 (s), 126.8 (d), 127.5 (d), 129.3 (d), 129.8 (d), 131.1 (d), 138.6 (s), 139.0 (s), 139.8 (s), 142.0 (s), 144.9 (s).

1e) $R^1$=H, $R^2$=H, n=1, m=1, Y=$CH_2$, $X^-$=$Br^-$ $^{13}$C-NMR DMSO-$d_6$ $\delta$: 17.0 (t), 35.0 (t), 50.9 (q), 59.9 (t), 60.5 (t), 110.8 (d), 119.0 (s), 121.7 (d), 122.4 (d), 126.5 (d), 127.5 (d), 129.2 (d)*, 131.5 (d), 138.9 (s), 139.5 (s), 139.7 (s) 143.5 (s), 144.7 (s).

*1 signal for two carbons

1f) $R^1$=H, $R^2$=H, n=3, m=0, $X^-$=$Br^-$ $^{13}$C-NMR DMSO-$d_6$ $\delta$: 21.7 (t), 25.4 (t), 35.0 (t), 50.8 (q), 59.2 (t), 63.2 (t), 110.7 (d), 119.1 (s), 121.8 (d), 122.5 (d), 126.6 (d), 127.4 (d), 129.2 (d), 129.3 (d), 131.6 (d), 139.0 (s), 139.6 (s), 139.8 (s), 143.6 (s), 144.8 (s).

Example 2

Synthesis of Ether Dimers
General Procedure (10 mmol Scale)

B-220 (or derivatives thereof), dihaloalkane and acetonitrile were heated at reflux for 20 h. The solid thus formed was isolated by filtration, washed with acetonitrile and dried.

2a) $R^1$=H, $R^2$=$CH_3$, n=2, Y=O, m=1, $X^-$=$Br^-$

Yield: 58%; $^1$H-NMR δ: 8.22 (d, 1H), 7.84 (s, 1H), 7.72 (m, 2H), 7.59 (s, 1H), 7.47 (d, 1H), 7.38 (t, 1H), 7.08 (d, 1), 4.85 (t, 2H), 4.09 (br. s, 2), 3.93 (m, 4H), 3.29 (s, 6H), 2.35 (s, 3H), 2.26 (s, 3H), 2.24 (s, 3H).

2b) $R^1$=9-Br, $R^2$=$CH_3$, n=2, Y=O, m=1, $X^-$=$Br^-$

Yield: 91%; $^1$H-NMR δ: 8.02 (d, 1H), 7.77-7.66 (m, 3H), 7.49 (s, 1H), 7.45 (d, 2H), 7.07 (d, 2H), 4.78 (t, 2H), 4.11 (br. s, 2H), 3.95-3.90 (m, 4H), 3.27 (s, 6H), 2.31 (s, 3H), 2.26 (s, 3H), 2.18 (s, 3H).

Biological Test

Tests of antiviral activity against human cytomegalovirus as described herein below were performed on a compound according to the invention, viz. the compound 1a of EXAMPLE 1. The reference compound termed B-220 is 2,3-dimethyl-6-(N,N-dimethylaminoethyl)-6H-indolo(2,3-b)quinoxaline, disclosed in European patent EP 0 238 459.

Test of Inhibitory Effects on Viral Infection

In order to assess whether targeting structural viral proteins would be as efficient as targeting viral transcription a modified plaque assay was set up, wherein one of the new antiviral agents was compared with already acknowledged antiviral agents that inhibit either HCMV's transcription [GCV (Cymevene, Roche) and PFA (Foscavir, AstraZeneca)] or infection [IVIg (IVIG CP, Biotest Pharma), an antibody].

In a 0 dpi (days post infection) experiment the antiviral agents and TB40/E were added simultaneously, thereby indicating how well the agents inhibit infection. The results from this experiment were obtained by comparing the amount of infected cells of the treated wells to that of the positive controls, thus calculating the inhibition of infection achieved by the agents in question. The experiment was repeated with the HCMV strain AD-169 and with a clinical isolate, respectively, with essentially the same results.

The inhibitory effect of the tested substances is shown in Table 1, as the % of inhibition of infection. These data are the results from plaque assays using strain AD169 and TB 40 of HCMV infected human lung fibroblasts.

TABLE 1

Inhibitory effect of tested substances as % inhibition of infection

| Substance | Inhibitory effect (%) |
| --- | --- |
| 1a | 100 |
| IVIg (reference) | 100 |
| B-220 (reference) | 20 |
| Leflunomide (reference) | 25-50 |
| Foscavir (reference) | 20-50 |
| Ganciclovir (reference) | 20-30 |

The results of the test indicate that the inventive compounds have excellent inhibitory effect on viral infection.

Test of Inhibition of HCMV Assembly and Egress

Infected human lung fibroblast cells (HL cells) were treated with the antiviral agent B-220 and with other reference substances, as shown in Table 2, and with inventive compound 1a in order to assess the effect of the inventive compounds on HCMV infection, assembly and egress.

The antiviral agents were added at 3 or 5 days post infection (dpi) in these experiments and left in culture until 7 dpi. Thereafter supernatant and crushed cells were transferred to new cell cultures over night and subsequently stained for IE expression. The results indicate how well the substances impede viral assembly and egress. More specifically, at 3 dpi the majority of the viral capsids are being assembled in the nucleus whereas at 5 dpi they are mainly receiving their tegumentation in the cytoplasm and some have commenced their secondary envelopment.

In Table 2 the inhibitory effect of the antiviral substances using the modified plaque assay system is shown. Several substances showed 100% inhibition of IE expression as measured by IE staining and no capsid formation was observed in the nucleus of the majority of the treated cells as observed by electron microscopy examination. The inventive compound termed 1a showed extremely good results matching the results obtained by Ganciclovir.

TABLE 2

Inhibitory effect of antiviral substances

| Substance | Inhibition 3 dpi (%) | Inhibition 5 dpi (%) |
| --- | --- | --- |
| 1a | 95-100 | 85-95 |
| B-220 (reference) | 65-85 | 65-80 |
| Leflonumide (reference) | 65-80 | 80-90 |
| Foscavir (reference) | 85-100 | 65-85 |
| Ganciclovir (reference) | 100 | 80-95 |

Mechanism of Action

Without wishing to be bound to any theory of the mechanism of action of the inventive compounds, it is noted that the tested inventive compound 1a shows very clear inhibition of IE expression. Furthermore, electron microscopy data indicate impairment of virus assembly. Indeed, the image analysis technique used to identify and quantify stable intermediate particles of HCMV indicated impairment of tegument protein binding to the viral capsid. Together these data show a high potential for the use of the inventive compounds in antiviral therapy. Also, by using the inventive compounds in combination with at least one other antivirally active agent, such as in a multidrug therapy, a synergistic effect is expected and the risk of acquired drug resistance may be reduced or avoided.

Toxicity

The inventive compounds did not show any toxicity as assayed by propidium iodide staining of cell cultures of infected and uninfected human lung fibroblasts. A concentration of compound 1a 10 times the one used in the experiments showed no toxicity during the time frame 0-7 dpi. The concentrations of compounds used in the viral experiments were at the μM level. Cellular toxicity for B-220 has been shown for concentrations above 100 μM.

Materials and Methods

Cell Culture

The human lung fibroblasts, HL-cells (MRC-5), used in these experiments were incubated at 37° C. and 5% $CO_2$ in a solution of MEM with Earle's and L-glutamine (from GIBCO) into which 10% Foetal Calf Serum (FCS) and 1% Penicillin and Streptomycin (PeSt) were added.

When the experiment commenced the HL cells were being kept in a Falcon cell culture flask of 175 cm². Trypsin and EDTA were used to loosen the cells from the cell culture flask when transferring them to 48-well multiwells (Becton Dickinson) for infection and incubation with the antiviral agents.

The cells were incubated until 50% confluence was reached under the same conditions as above and were used up to the 26$^{th}$ passage.

Infection of Cells with HCMV

The HL cells were infected with HCMV, viral strain TB 40/E [an endothelial adapted clinical isolate (UR1814) kindly provided by Prof. G. Jahn] and viral strain AD-169, respectively, at a multiplicity of infection (MOI) of 0.02 and incubated until 3 or 5 days post infection (dpi) at 37° C. and 5% $CO_2$ in the same mediums as above. Some cells (for the 0 dpi experiment) were simultaneously exposed to the antiviral agents (see below). The negative controls were left uninfected.

Exposing the Cells to Inhibitors and Antiviral Agents

The existing medium (in the 3 and 5 dpi experiments) was changed and new medium added, with inhibitors and antiviral agents at different concentrations. However this was done simultaneously to the infection in the 0 dpi experiment and left to incubate until 1 dpi. The medium containing IVIg was incubated for an hour with the virus on ice prior to being added to the cells.

Modified Plaque Assay

In the 3- and 5 dpi-experiments the supernatant of the MRC-5 cells was transferred to uninfected cells to assess the amount of excreted virus. The remaining cells were given new medium and crushed with glass marbles by shaking the multiwells on an IKA-Vibrax-VXR at 300 shakes pm for 10 min. Thereafter the cellular debris was transferred to uninfected cells to be able to evaluate the amount of infectious intracellular viral particles.

After letting the viral particles infect the new cells for approximately one hour the medium was changed, thus washing away the cellular debris.

In the 0 dpi-experiments the cells were fixed immediately 1 dpi (in accordance with the procedure explained below).

Positive controls (untreated infected cells) and negative controls (untreated uninfected cells), were treated, respectively, as above.

Immunofluorescent Staining of the Cells

The new HL cells (in the 3 and 5 dpi experiments) were fixed the following day with 3% paraformaldehyde (PFA) for 15 min at room temperature (RT). To make the cells permeable, 0.3% TritonX in Phosphate Buffer Saline (PBS) was used for 15 min incubation at RT followed by blocking of the background with background block from DAKO for 20 min at RT, with an amount just large enough to cover the entire surface. Thereafter all multiwells were incubated with primary antibodies (mouse), diluted to 1:100, against immediate early antigen (IEA, Antigene) for 45 min at 8° C. Subsequently the cells were incubated with secondary antibodies, rabbit anti mouse FITC (Dako Cytomation), diluted to 1:100, for 45 min at 8° C. and simultaneously stained with DAPI (Sigma), diluted to 1:250 DAPI is a chemical substance that stains the nucleus of the cells.

The positive and negative controls, of both cell types, were treated, respectively, as above.

Immunofluroscence Microscopy Analysis

The cells were analyzed by fluorescent microscopy using a Nikon Eclipse TE 2000-U. The amount of cells expressing IEA, in two different parts of the well, was counted by the naked eye and compared to the total amount of cells (indicated with DAPI), in those same parts. These values were used to appreciate the percentage of infected cells in each well from which the amount of inhibition achieved by the different substances was calculated. This method of calculating the percentage of infected cells in two parts of a well and then applying it to the entire well was chosen since the total amount of cells in a well would be impossible to count manually.

The invention claimed is:

1. A compound of formula (I)

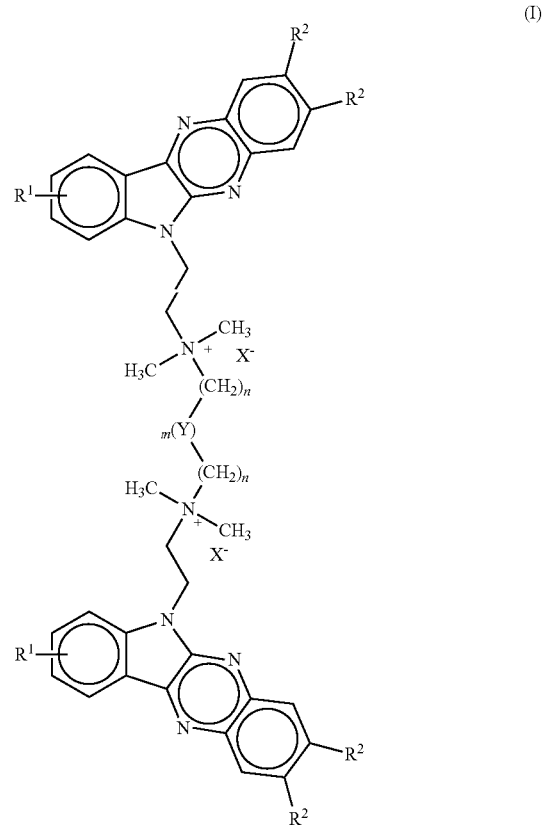

wherein
$R^1$ is selected from H, F, Cl, Br, $CF_3$, $C_1$-$C_6$ alkoxy and OH;
$R^2$ is selected from H and $C_1$-$C_6$ alkyl;
n is 1-12;
m is 0 or 1; and
Y is selected from $CH_2$, $NR^3$, $(NR^3R^4)^+X^-$, O and S;
$R^3$ and $R^4$ are independently selected from H and $C_1$-$C_4$ alkyl; and
$X^-$ is selected from pharmaceutically acceptable anions.

2. A compound according to claim 1, wherein $R^1$ is selected from H, F, Cl, Br, $CF_3$, $OCH_3$ and OH.

3. A compound according to claim 1, wherein $R^2$ is selected from H and $CH_3$.

4. A compound according to claim 1, wherein X" is selected from Cl⁻, Br⁻, methanesulfonate, toluenesulfonate, acetate, citrate and maleate.

5. A compound according to claim 1, wherein m is 0.

6. A compound according to claim 1, wherein m is 1.

7. A compound according to according to claim 6, wherein Y is O.

8. A compound according to claim 1, wherein n is 4-10.

9. A compound according to claim 1, wherein n is 1-3.

10. A method of preparing a compound according to claim 1, by reacting a compound of formula (II)

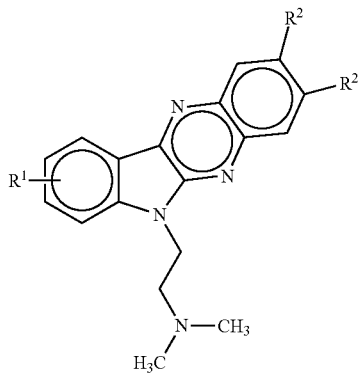

with a compound of formula (III)

$$L(CH_2)_n(Y)_m(CH_2)_nL \quad \text{(III)}$$

wherein $R^1$, $R^2$, Y, m and n are as defined in claim 1; and

L is a leaving group; in a solvent or mixture of solvents.

11. A method according to claim 10, wherein the leaving group is selected from Cl, Br, methanesulfonyl and toluenesulfonyl.

12. A pharmaceutical composition comprising a compound according to claim 1, and a pharmaceutically acceptable excipient.

13. A pharmaceutical composition according to claim 12, for use as an antiviral drug.

14. A method of treating a herpes virus infection in a vertebrate animal in need of such treatment comprising administering a pharmaceutical composition according to claim 12 to the animal.

* * * * *

UNITED STATES PATENT AND TRADEMARK OFFICE
CERTIFICATE OF CORRECTION

| | | |
|---|---|---|
| PATENT NO. | : 8,076,341 B2 | Page 1 of 1 |
| APPLICATION NO. | : 12/161081 | |
| DATED | : December 13, 2011 | |
| INVENTOR(S) | : Mohammed Homman et al. | |

It is certified that error appears in the above-identified patent and that said Letters Patent is hereby corrected as shown below:

Title page, item (75) Inventors: "Engovist" should read --Engqvist--.

Title page, insert item (56) foreign application priority data: --Sweden 0600134-1 01/23/2006--.

Signed and Sealed this
Thirteenth Day of March, 2012

David J. Kappos
*Director of the United States Patent and Trademark Office*